United States Patent [19]
Marsh, Jr.

[11] 3,953,406
[45] Apr. 27, 1976

[54] WATER-INSOLUBLE, SWELLABLE POLYURETHANES

[75] Inventor: Harold E. Marsh, Jr., La Canada, Calif.

[73] Assignee: California Institute of Technology, Pasadena, Calif.

[22] Filed: Jan. 26, 1973

[21] Appl. No.: 326,768

[52] U.S. Cl.............. 260/77.5 AM; 252/182; 260/2.5 AD; 260/77.5 AP; 260/859 R; 424/78
[51] Int. Cl.²........... C08G 18/48; A61K 31/785
[58] Field of Search............. 260/77.5 CR, 2.5 AD, 260/859, 77.5 AP, 77.5 AM; 252/182

[56] References Cited
UNITED STATES PATENTS

| | | | |
|---|---|---|---|
| 3,284,415 | 11/1966 | Horvath | 260/77.5 CR |
| 3,350,362 | 10/1967 | Potts et al. | 260/77.5 CR |
| 3,351,676 | 11/1967 | Saunders et al. | 260/77.5 CR |
| 3,368,988 | 2/1968 | Sekmakas | 260/77.5 CR |
| 3,551,472 | 12/1970 | Siebert | 260/77.5 CR |
| 3,659,003 | 4/1972 | Johnsen et al. | 260/77.5 CR |
| 3,660,355 | 5/1972 | Johnsen et al. | 260/77.5 CR |
| 3,778,332 | 12/1973 | Butler et al. | 260/2.5 AD |
| 3,805,532 | 4/1974 | Kistner | 260/2.5 AD |
| 3,806,474 | 4/1974 | Blair | 260/2.5 AD |
| 3,821,136 | 6/1974 | Hudgin et al. | 260/77.5 AP |
| 3,822,238 | 7/1974 | Blair et al. | 260/75 NK |

*Primary Examiner*—H. S. Cockeram
*Attorney, Agent, or Firm*—Marvin E. Jacobs

[57] ABSTRACT

This application discloses lightly cross-linked, swellable polymers including both oleophilic and hydrophilic chains. The polymers have an unusually high capacity for absorbing from solution large organic molecules containing polar groups. The polymers are free of components leachable in the gastrointestinal tract, have low oral toxicity and dermal sensitivity and can be utilized in vitro or in vivo to absorb lipids from bile. The polymers have exhibited absorption as high as 309% total and 59% solids from a concentrated micellar bile. Cholesterol, lecithin and sodium cholate were confirmed in the absorbate by thin-layer chromotography.

11 Claims, 2 Drawing Figures

WATER-INSOLUBLE, SWELLABLE POLYURETHANES

ORIGIN OF THE INVENTION

The invention described herein was made in the performance of work under a NASA contract and is subject to the provisions of Section 305 of the National Aeronautics and Space Act of 1958, Public Law 83-568 (72 Stat. 435; 42 USC 2457).

BACKGROUND OF THE INVENTION

1. Field of the Invention

The present invention relates to novel polymeric compositions and to their use in absorption of oils and, more particularly, this invention relates to the absorption of polar-substituted organic compounds from aqueous suspension or solution.

2. Description of the Prior Art

The well-known cholesterol problem in the Western World is believed to originate, at least to some extent, from the high fat content in the diet. Fatty degeneration of the inmost wall of the artery, atherosclerosis, is a common ailment linked to high levels of serum cholesterol. Gallstones, or the deposition of cholesterol and bile pigments in the gallbladder, is also believed to result from excessive levels of cholesterol in the hepatic bile. Another theory of gallstone formation is based not only on excessive cholesterol levels, but also on the ability of the gallbladder to properly dispel bile into the bile duct. Both theories recognize that high cholesterol concentration presents problems.

Enterohepatic circulation involves the movement of bile constituents from the liver, through the gallbladder, the intestines, absorption from the intestines, and passage back to the liver.

Many types of dietary materials or medicines have been reported effective in the removal of bile acids from the enterohepatic circulation, resulting indirectly in a reduction in serum and tissue cholesterol, the parent sterol of bile acids. Included in these materials are dextran and cellulose ion exchange resins, lignin, other polysaccharides, Cholestyramine, and a synthetic organic polymer composed of a basic anion exchange copolymer of tetraethylenepentamine and epichlorohydrin with approximately 1 out of 5 amine nitrogens protonated. Evidence has just recently been reported for the nonsurgical removal of gallstones by the feeding of large amounts of the bile acid, chenodeoxycholic acid.

Present medicinal approaches to reducing serum and tissue cholesterol levels in man are indirect. Intestinal reabsorption of bile acids, which are liver-produced derivatives of cholesterol, is reduced by administration of non-absorbable bile acid-binding polymers. The binding is accomplished by means of ion exchange on polymers bearing amine groups. For example, materials under study include various primary, secondary and tertiary ethylamine adducts of cellulose and other polysaccharides, a copolymer of tetraethylene pentamine and epichlorohydrin, and a quaternary ammonium styrene-divinylbenzene copolymer. The last polymer, known as Cholestyramine, has been in use medically for a number of years.

In a first approach to the development of a dietary additive capable of absorbing significant amounts of cholesterol from the dietary tract, a class of lighty cross-linked hydrocarbon, swellable polymers were developed. These polymers are the subject of my copending application Ser. No. 228,229, filed on Feb. 22, 1972. Though these polymers demonstrated significant absorption of diverse types of oils, when tested with a model bile, there was no absorption of significant amounts of cholesterol and/or bile acid from the solution. It was determined that the absorption of lipids from bile is a wholly different process than absorption directly from the same lipids in bulk or simple solution state.

A hypothesis was first generated to explain the anomalous behaviour of the oil absorbing polymers. The model bile is composed of water and the lipids, lecithin, cholic acid, and cholesterol; the total lipid content is about 50% by weight. Although this solution appears to be completely homogeneous, even microscopically, the distribution of these four components is not uniform on a molecular scale. The water is continuous but the lipids exist in clusters of a few molecules each. These clusters are called micelles. A stable structure is produced in micelles because of the existence of both polar and nonpolar groupings in the two lipids lecithin and cholic acid. In both molecules, the nonpolar groupings are hydrocarbon. Hydrocarbons and water are generally immiscible. On the other hand, polar organic compounds tend usually to be very soluble in water. Thus, the structure envisioned for micelles is a tiny sphere in which these several molecules are oriented so as to surround a hydrocarbon interior by a polar shell.

Conceptually, there is no reason to expect a micelle's polar surface to have affinity for the hydrophobic surfaces of immersed oil-absorbing polymer particles. More to be expected is the operation of the polar shell as a barrier which either prevents or greatly reduces the opportunity for hydrocarbon groups inside the micelle to make contact with the polymer.

The formation of mixed micelles is of primary importance in the digestion of fats. Micelles are molecular aggregates composed, in this case, of bile salts, lecithin and cholesterol. A highly polar exterior portion of the micelle is water-soluble while the nonpolar interior is lipid-soluble. A relatively nonpolar material like cholesterol is solubilized by the micelle through the affinity of the lipophilic interior for cholesterol and the hydrophilic exterior for water, the continuous phase.

An understanding of the role of the mixed micelle in lipid digestion and assimilation leads to a theory of a polymer formulation — formulation for materials with a high affinity and absorptive capacity for lipids. It is noted that the polar exterior of the micelle shields to some extent the nonpolar interior from the attraction of oleophilic materials. Therefore, micellar cholesterol or other nonpolar lipids would not even be aware of the presence of nonpolar materials outside the micelle. This would appear significant when considering polymers for lipid absorption.

A polymer comprised totally of hydrophilic chains would have great affinity for the continuous phase and the polar exterior of the micelle. However, disruption of the micelle prior to or during absorption would expose nonpolar constituents, for which the polymer would have no affinity. On the other hand, a totally oleophilic polymer would have no affinity for the polar groups of lipid molecules, nor would they have sufficient affinity for their hydrocarbon chain parts to draw the highly hydrophilic ends out of the aqueous phase.

SUMMARY OF THE INVENTION

A very effective polymeric absorber capable of absorbing fatty substances from an isotropic micellar bile solution is provided according to the invention by synthesizing a lightly cross-linked, swellable, network polymer containing controlled amounts of both hydrophilic and hydrophobic chains. The polymers are capable of absorbing both water and oily or fatty substances. As a result of this property they are also able to absorb significant amounts of lipids from micellar bile solutions including not only bile acids but cholesterol and lecithin.

The basis for this high absorption is believed to be the high affinity of lipid polar groups for water in addition to that of their larger aliphatic parts for the hydrocarbon polymer chains. High polar group-water affinity is the force also which makes possible the solution of high concentrations of properly proportioned lipids in water. In such solutions water is the continuous phase, and all of the lipid molecules are in micelles which are submicroscopic clusters arranged so that the large hydrocarbon tails of the molecules are surrounded by a sheath composed of their polar groups.

The interaction between micelles and hydrocarbon polymers that might be expected on the basis of the above discussion would be limited to the polymer surface. Lipid molecules coming into close contact with polymer chains will be unable to diffuse into the polymer because of the force retaining the polar groups in the aqueous phase. At equilibrium a polymer particle probably would resemble a very large micelle, a hydrocarbon body surrounded by a polar sheath. Therefore, in order for a polymer to be able to absorb larger amounts of bile lipids, it must be able to absorb water, as well as oils, so as to attract both parts of lipid molecules.

Absorption rate is inversely related to particle size, the fastest rates being exhibited by small particle size of no more than 1 mm. The swellability should be no less than 2 of the micellar solution. The maximum swellability is only limited by the requirement of maintaining a lightly cross-linked network during passage through the gastrointestiinal (G.I.) tract. In some other uses to be discussed, biodegradability of the network may be advantageous. The amount of polar organic compound absorbed on a dry basis is at least about 10 percent. The proportion of hydrophilic chain should be at least 1 and no more than 90 percent of the polymer network. The amount of cross-linking is controlled to provide the swellability, absorption and stability needed for the intended usage.

The process for synthesizing these polymers includes steps for insuring that no potentially harmful or assimilable substance will be released in the G.I. tract. In a preferred method, the polymer is prepared from a solution in a common solvent of a functionally terminated liquid oleophilic prepolymer and a functionally terminated hydrophilic prepolymer containing a trifunctional cross-linking agent and a difunctional curing agent. Post-polymerization workup requires an extraction step to remove the sol fraction. The solution in common solvent assures an even distribution of the mixed chain throughout the polymer network. The polymers are lightly colored solids having no perceptible flavor and do not show measurable decomposition when exposed to solutions of pH 2 and pH 8 for 1 week.

These and many other attendant advantages of the invention will become apparent as the invention becomes better understood by reference to the following detailed description when considered in conjunction with the following drawings.

DESCRIPTION OF THE PREFERRED EMBODIMENTS

Figure 1:
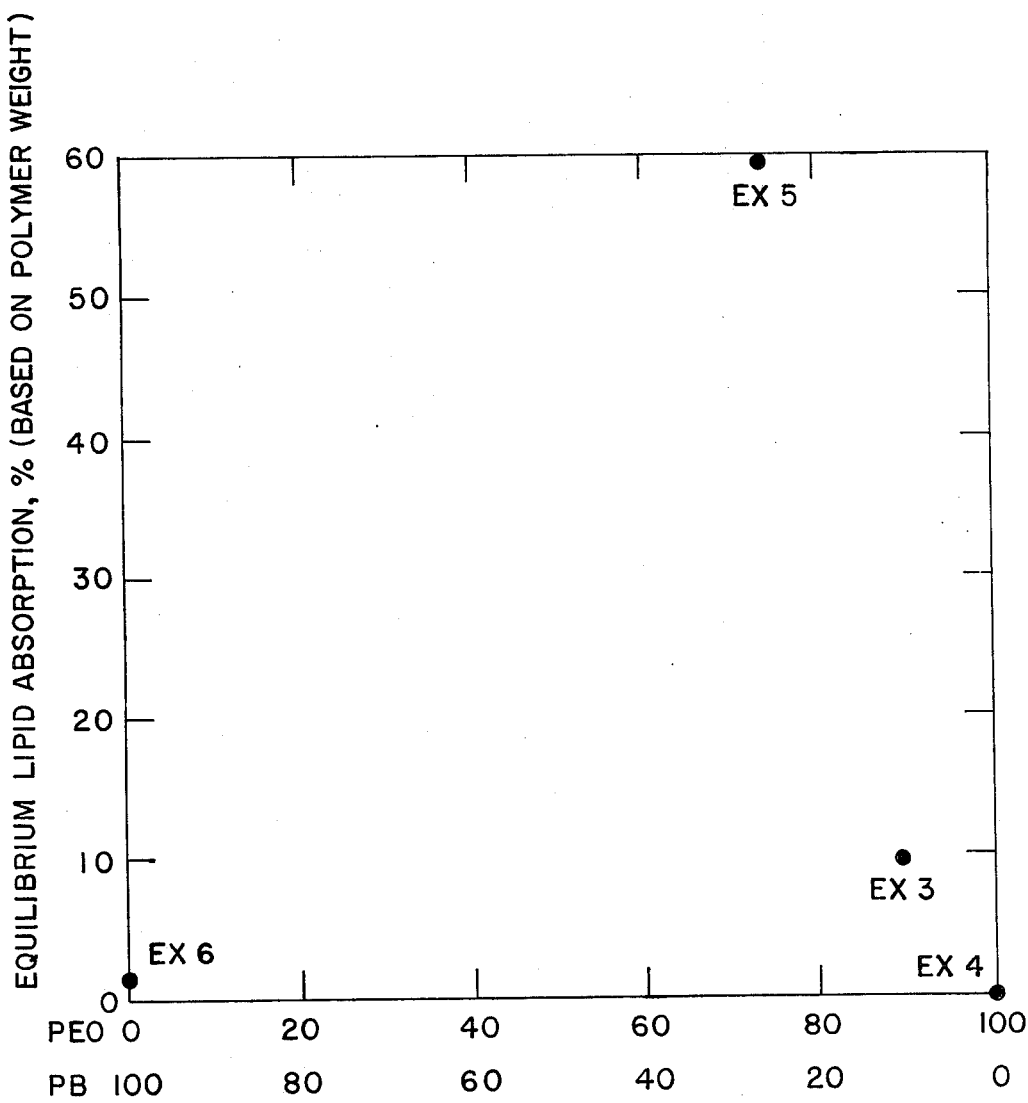
FIG. 1 is a graph showing the effect of relative polyethylene oxide (PEO) and polybutadiene (PB) concentration as abscissa on the equilibrium lipid absorption as ordinate.

The polar compounds capable of being absorbed by the network polymers of the invention are generally high molecular weight organic compounds containing at least 10 carbon atoms and being substituted with at least one polar group such as hydroxyl, ether, ester, inorganic acid, carboxyl. The organic compound may be synthetic or of vegetable or animal origin and may be aliphatic in nature such as glyceryl esters of $C_{16}$ — $C_{24}$ aliphatic fatty acid or alicyclic in character such as steroids which include sterols, bile acids, saponins and the sex hormones.

The oleophilic chain segments should have a minimum chain length of 25 carbon atoms to provide sufficient nonpolar force to attract the hydrocarbon portion of the molecule to be absorbed. The oleophilic chains can have molecular weights up to 100,000 or more. However, since such polymers are fairly viscous, they are more difficult to homogeneously disperse and cross-link with the hydrophilic chains. Liquid prepolymers having molecular weights from 1,000 to 5,000 and preferably 2,000 to 3,000 are most effective in the synthesis of this invention.

Representative prepolymers are polymers or copolymers of $C_2$ to $C_8$ monounsaturated aliphatic hydrocarbon monomers such as polyethylene, polypropylene, polybutylene, ethylene-propylene, or of $C_4$ to $C_8$ dienes such as polybutadiene, polyisoprene, polypentadiene, polyhexadiene, or hydrogenated derivatives thereof. The hydrocarbon prepolymers are absent groups toxic to the animals. Preferred hydrocarbon prepolymers are the liquid polymeric butadienes which are readily available with functional termination such as hydroxyl or carboxyl.

The hydrophilic chains are provided by prepolymers having the same molecular weight parameters discussed above with respect to the oleophilic chains. The hydrophilic chains contain a polar group capable of binding water such as hydroxl, carboxyl, inorganic acid such as sulfonic or phosphonic, ether, ester, thiol, amino. Representative prepolymers are polyvinyl alcohol, polyvinylpyrrolidone, polysaccharides, polyacrylic acid, polyacrylamides, cellulose, alginates, polyamides, polyesters, monoesterified glycerol polymers, certain polypeptides, polyethylene hydrazine and polyalkylene oxide polymers such as polypropylene oxide and polyethylene oxide. The latter are preferred due to their stability, hydroxyl chain termination, absence of irritating or toxic components and the ready availability in the desired 1,000 to 5,000 molecular weight range.

The mixed prepolymers can be joined into a network by known cross-linking mechanisms such as radiation, solvent run to calculate $R_f$ value. The paper was then allowed to dry thoroughly. The paper was then placed in a developing chamber laid horizontally on bench top which had benzene in it. The chamber was sealed with tape and allowed to reach equilibrium (10 minutes). The development was begun by standing the chamber in the vertical position. The development was stopped when the solvent reached the 10 cm mark by placing the chamber back in the horizontal position. The chromatograph was then allowed to thoroughly dry. It was then spayed with a sulfuric acid/dichromate solution and placed in a 200°C oven for 10 minutes to visualize the spots by charring. Spots were visible on each sample at the same $R_f$ value of the pure cholesterol confirming the presence of cholesterol in the polymer extract solvent.

A series of network polymers containing varying amounts of the mixed chains were prepared according to the following general procedure.

Experience has shown the exclusion of moisture from the prepolymers is essential for cure. With this in mind, Carbowax (polyethylene glycol) was melted in an oven at 140°F and then rotovaced at 212°F and 3 mm Hg for 3 hours. It was stored in a dry box.

Carbowax and the liquid hydroxy-terminated polybutadiene, either Telagen or Butarez, were heated to aove 140°F in separate beakers prior to mixing. After mixing of the prepolymers, TMP was added and allowed to melt. Sufficient solvent for solution polymerization, generally 100 or 150 ml of dioxane or benzene, was added to keep the solution clear. A stoichiometric amount of dimer acid diisocyanate (DDi) and FeAA, when it was used, were then mixed in completely. The beaker was covered with aluminum foil and cured in the oven at 160°F for 3 days. For sme formulations, e.g., the polymers prepared without catalyst, longer curing times were required.

Two extraction procedures have been used for removal of the sol fraction or the noncross-linked portion of the polymer. The first and most effective method, effective in terms of time required and cleanup obtained, was the automatic Soxhlet extraction. A 5-day Soxhlet extracton was normally followed by many soak extractions in a suitable solvent. The Soxhlet extractor, although very effective, was restricted to rather small samples. When larger samples of polymer were required, repetitive soak extractions with fresh solvent was necessary.

Experiments were performed to measure qualitatively the effectiveness of various solvents in removing sol fraction. Acetone, dioxane, and benzene were effective in sol removal while water, ethanol, and isopropanol were totally ineffective. All polymers used in absorption studies were extracted with either dioxane or benzene.

The polymers had the following composition.

TABLE 1

| Example | PEG, % | HTPB % | Type |
|---|---|---|---|
| 2 | 75 | 25 | Telagen SHTPB (Saturated HTPB) |
| 3 | 90 | 10 | Do |
| 4 | 100 | 0 | Butarez (HTPB) |
| 5 | 75 | 25 | Do |
| 6 | 0 | 100 | Do |
| 7 | 35 | 65 | Telagen |
| 8 | 75* | 25 | Butarez |
| 9 | 75* | 25 | Do |

*NCO/OH = 1.15

The purity of the network polymer, or the lack of sol fraction in the extracted sample, was determined by spotting 100 μl of the extract on TLC paper, then developing with benzene and charring at 180°C. A "clean" polymer gave little if any coloration on the chromatogram, whereas, a "dirty" polymer gave black spots or streaks characteristic of certain poly constituents, normally the polybutadiene prepolymers which were difficult to remove.

Thin-layer chromatograms spotted with 100 μl of sample were used as the criterion for cleanup in all extraction operations.

Model bile for absorption studies was prepared with the following composition on a weight percent basis:

| | |
|---|---|
| sodium cholate | 25 |
| egg lecithin (crude) | 20 |
| cholesterol | 0.5 |
| water (pH 10) | 54.5 |

This formulation differs considerably from that reported for normal human bile:

| | | |
|---|---|---|
| bile salt | 5.4 | (considered here as sodium cholate) |
| lecithin | 3.0 | |
| cholesterol | 0.5 | |
| water | 91.1 | |

It was impossible to prepare an isotropic bile solution of the human bile composition reported above. In order to totally dissolve the desired amount of cholesterol, large amounts of lecithin and sodium cholate were required. This problem is probably attributable to the high concentration of impurities in the egg lecithin.

Polymer samples were used in two particle size classes for lipid absorption test, chunk (about 6 mm) and ground (about 1 mm). Contact times for polymer samples with model bile ranged from 5 minutes to 220 hours.

Samples were weighed before contact, after contact and after subsequent removal of absorbed water by vacuum drying.

The absorption capacity of polymers for lipids from micellar solutions is highly dependent upon polymer structure. This result is illustrated in FIG. 1. In 147 hours, polymer Ex. 4 (100/0 PEO/PB) absorbed 271% total material, but after the water was removed, only 0.3% lipid residue remained. In 144 hours, polymer Ex. 6 (0/100 PEO/PB) absorbed only 3% total, 2/3 of which was lipid. In corresponding contact times, polymers with intermediate compositions, Ex. 3 (90/10) and Ex. 5 (75/25), absorbed much more lipid, 9.5% and 59% respectively. Reliable data are not available for polymers whose compositions lie between PEO/PB ratios of 75/25 and 0/100 because of difficulties in grinding these more rubbery materials in the laboratory. This obstacle will be eliminated in future work, and it can be expected from the data in FIG. 1 that higher absorption capacities will be measured.

free radical cure or condensation curing. Condensation cure is preferred since the amount of cross-linking can readily be controlled by the type and amount of cross-linking agent.

Suitable functional group pairs are hydroxyl-carboxyl (ester), epoxy-carboxyl (ester), amino-carboxyl (amide), amino-isocyanate (urea) and hydroxyl-isocyanate (urethane). Due to the stability of the urethane group, the ready availability of hydroxyl terminated prepolymers of both types and the previous use of urethane prosthetics demonstrating safety in clinical use, the urethane group is the linkage of choice in forming the network polymers of the invention.

The polymerizaton mixture must contain some trifunctional cross-linking agent but may also contain a difunctional curing agent and may also contain a monofunctional modifier to control cross-linking and chain extension. A catalyst may also be present to accelerate polymerization.

In the case of a urethane cure, the curing agent can be a diisocyanate such as toluene diisocyanate (TDI), dimer acid diisocyanate, hexamethylene diisocyanate and 4,4'-methylene di-o-tolyldiisocyanate. The curing agents may also be of prepolymer length, suitably 1,000 to 3,000 molecular weight. Such materials are readily synthesized by prereacting a portion of hydroxy-terminated butadiene with a diisocyanate such as TDI. A suitable triol cross-linking agent is trimethylol propane (TMP), 1,2,6-hexane triol, glycerol. Any known urethane catalyst can be used such as ferric acetyl acetonate or stannous octoate. The ratio of NCO to OH can be any ratio between gelling range of the polymerization composition, but the preferred range is between about 1.0 to about 1.15.

Dioxane is a suitable solvent for both polyethylene oxide (PEO) and hydroxyl terminated polybutadiene (HTPB). The solution of the prepolymers, curing agent, cross-linking agent and catalyst is heated to cure and cross-link the polymer. After cure the sol fractions were removed by repetitive extraction.

The following example illustrates the synthesis and test of a representative network, mixed chain polymer.

EXAMPLE I

1. Polymer Preparation — Synthesis.

Hydroxyl terminated polyethylene oxide (Carbowax 1000) and unsaturated hydroxyl-terminated polybutadiene (Telagen U) were mixed together in a ratio of 75/25 by weight respectively. Trimethylol propane (TMP) was used as network crosslinker with the ratio of triol to total hydroxyl being 0.25. Toluene diisocyanate (TDI) was used as curing agent with NCO/OH = 0.95. Carbowax and Telagen were weighed out in plastic beakers and heated on a hot plate to 110°F until the mixture was clear. TMP was added and allowed to melt and was also mixed in until clear. TDI was weighed out in a separate beaker and 0.017 parts of ferric acetylacetone (FeAA) catalyst were added and allowed to dissolve. This mixture was then added to the Carbowax, Telagen, TMP mixture. 200% of bulk weight solvent (dioxane) was added to the mixture to keep everything in solution. After the sample was completely mixed by hand with a spatula, it was then covered with aluminum foil and placed in a 160°F oven for cure which took 5 days.

2. Extraction — Removal of Sol Fraction of Non-network Material.

A. Soxhlet Extraction.

Part of the cured sample from Step 1 was placed in a thimble of soxhlet extractor with Benzene/Ethanol (68:32) as solvent in a boiler and was extracted for five days. After extraction, the solvent was removed from the polymer by first air drying and then vacuum drying. Sol/Gel for this system was 2.7.

B. Soak Extraction.

Another part of the cured sample from Step 1 was placed in a beaker of Benzene/Ethanol (68:32) and allowed to soak extract for 10 days. The solvent was poured off the swelled sample each day and new solvent was added. After soak extraction, the sample was also air and vacuum dried. Sol/Gel was 11.8. Some error was found with this system as part of the gel fraction was removed with each solvent change.

3. Absorption Capacity.

A. Model Bile Absorption.

A weighed amount of each sample (2A) of soxhlet extracted and (2B) soak extracted was placed in model bile (cholesterol 0.5%, sodium cholate 25.0%, Egg Lecithin 20.0%, water 54.5%) and allowed to absorb bile for 80 days. Each sample was then thoroughly washed under water to remove surface or non-absorbed material, then quickly dried under $N_2$ purge. The sample was then weighed to obtain swelled capacity. Samples were placed in a vacuum overnight to remove water that had been absorbed and were then reweighed.

|  | Bile Absorption | Absorption After Drying |
|---|---|---|
| 2A Soxhlet Extracted | +221.0% | +16.2 |
| 2B Soak Extracted | +203.0% | +37.6% |
| B. Water Absorption. | | |
|  | Water Absorption | |
| 2A Soxhlet Extracted | 196% | |
| 2B Soak Extracted | 255% | |

4. Extraction of Absorbed Material.

Each of the dried bile absorbed samples was placed in a bottle of dioxane to soak extract the absorbed material out of the polymer. The soaking was for 3 days. The sample was then removed from the first solvent soak and placed in fresh solvent to continue soak extraction. The first solvent with extract was saved for analysis.

5. TLC Analysis for Cholesterol Content.

During previous work a method to check for cholesterol content of bile fluid was developed using thin-layer chromatography. It was found that by overspotting 10 $\mu l$ quantities of a 1 mg/ml solution of bile fluid in ethanol for 20 times, drying between each spot, after developing with benzene on a silica gel impregnated glass paper (ITLC-SG), good separation of cholesterol could be found at an $R_f$ value of 75. This was repeated with pure cholesterol and found to be the same.

6. Analysis of Abosrbed Material Extract.

The first soak extraction solvent from the bile absorbed samples was analyzed for cholesterol content on TLC plates. First a 10 $\mu l$ spot from each solvent sample was placed on the base of the paper, three spots for each sample. The spots were allowed to dry and then were overspotted again and allowed to dry. This was repeated until a 200 l spot was applied. Two more spots of 10 $\mu l$ of pure cholesterol 1 mg/ml in ethanol were applied to be used as reference spots. The spot line was marked at the side of the paper and another line marked at 10 cm up the paper to mark the distance of important finding in FIG. 1 is the systematic dependence of capacity on structure. It is clear that somewhere between the points represented by Ex's. 5 and 6 there is a maximum.

One small set of tests was run to make a preliminary examination of the potential stability of this type of polymer in the digestive tract. Samples of the polymer of Ex. 5 were exposed to aqueous solutions of pH 2 and 8 for 99 hours and were then tested for lipid absorption at 30 minutes contact with model bile. No measurable change occurred.

Short term absorption capacity can be improved by reduction in polymer particle size. Almost 24 hours were required for a polymer of Ex. 5 in chunk form (∼ 6 mm) to absorb the 10% achieved in 5 minutes by the same polymer ground to ∼ 1 mm size. All three liquids used to make the micellar test solutions, cholesterol, sodium cholate, and lecithin, were found in absorbates. There was no evidence of selectivity related to lipid structure.

After many repetitive extractions with 1,4-dioxane and benzene, small samples of the ground polymer of Ex. 5 were sampled by three researchers for flavor and consistency. It was agreed that the polymer had no flavor and a somewhat gritty texture, but certainly not nauseous. In appearance the ground polymer (1 mm) is light orange. Smaller particles would probably show even less coloration.

After many extractions in 1,4-dioxane and benzene and judged free of sol fraction by TLC (char at 180°C), the polymer of Ex. 5 (75/25: PEG/Butarez) was investigated for its ability to absorb model bile. The results are presented in Table 3.

TABLE 3

Rate of Absorption of Model Bile by Ground Polymer (Ex. 5)

| Contact Time | % Absorption Wet | % Absorption Dry | Ratio % Absorption Wet / % Absorption Dry |
| --- | --- | --- | --- |
| 5 min. | 58.9 | 5.8 | |
| | 54.2 | 4.1 | ∼ 10 |
| | 56.4 | 5.3 | |
| 30 min. | 87.3 | 8.1 | |
| | 84.8 | 8.4 | ∼ 10 |
| | 84.7 | 7.8 | |
| 2 hr. | 111 | 14.2 | |
| | 103 | 12.5 | ∼ 8 |
| | 110 | 13.6 | |
| 6 hr. | 136 | 20.0 | |
| | 124 | 21.1 | ∼ 6 |
| | 127 | 19.3 | |
| 16 hr. | 155 | 27.0 | |
| | 170 | 28.1 | ∼ 6 |

TABLE 3-continued

Rate of Absorption of Model Bile by Ground Polymer (Ex. 5)

| Contact Time | % Absorption Wet | % Absorption Dry | Ratio % Absorption Wet / % Absorption Dry |
| --- | --- | --- | --- |
| | 168 | 28.8 | |
| 24 hr. | 192 | 29.3 | |
| | 192 | 30.2 | ∼ 6 |
| | 196 | 28.3 | |
| 144 hr. | 309 | 57.9 | ∼ 5 |
| | 305 | 59.4 | |

Bile Absorption by the polymers of Ex. 5 after contact with buffers simulating intestinal pH was conducted. Ground samples (1 mm) of the polymers of Ex. 5 were contacted with buffers of pH 2 and 8 for 99 hours. After buffer contact the dried samples were allowed to absorb model bile for 30 minutes. A comparison of absorption by buffer contacted polymers and material without exposure to buffer is presented in the following Table.

TABLE 4

| Contact Time | Unexposed Polymer % Absorption | | pH 2 Exposed Polymer % Absorption | | pH 8 Exposed Polymer % Absorption | |
| --- | --- | --- | --- | --- | --- | --- |
| | Wet | Dry | Wet | Dry | Wet | Dry |
| 30 min. | 87.3 | 8.1 | 75.3 | 9.3 | 85.9 | 10.0 |
| | 84.8 | 8.4 | 80.8 | 7.7 | | |
| | 84.7 | 7.8 | | | | |

The absorptivity, stability, toxicity and rate of absorption studies indicate that the network polymers of this invention will find use as a dietary additive useful in clinical suppression of cholesterol level. The control is more direct. The polymers are capable of binding both cholesterol and bile acids while present therapeutic materials only bind bile acids whih are derivatives of cholesterol.

It is expected that work now in progress will result in significant increase in the absorptivity of these polymers especially by modification of the cross-link density which should be no less than on cross-link per every 4,000 backbone chain atoms and optimization of the hydrophilic-oleophilic ratio. The effect of a dosage amount of 15 grams of the polymer of Ex. 5 is calculated below:

According to the literature, the highest concentration of bile acids in the upper region of the intestinal lumen soon after emptying the gall bladder is about 15–45 meq/liter.

Assume 30 meq/liter:

$$\left(\frac{30 \text{ meq}}{\text{liter}}\right)\left(\frac{400 \text{ mg}}{\text{meq}}\right) = \frac{12{,}000 \text{ mg}}{\text{liter}} = \frac{12 \text{ gm}}{\text{liter}} \text{ sodium cholate}$$

Model Bile:

$$\frac{100 \text{ gm}}{400 \text{ ml}} \left(\frac{10^3 \text{ ml}}{\text{liter}}\right) = \frac{250 \text{ gm}}{\text{liter}} \text{ sodium cholate}$$

Assume same absorption in intestine as in model bile:

The maximum absorptions that were measured were obtained with the polymer of Ex. 5 which is composed of 75 parts PEO and 25 parts PB plus curing ingredients. Total absorption (water plus lipids) at equilibrium measured on a number of samples of this type of polymer ranged from 305 to 309% based on original polymer weight. Lipid absorption (measured after removal of absorbed water) measured from 57 to 59.4%. These measurements were made after from 140 to 150 hours of contact. After 5 minutes, the corresponding values were 54.2 to 59.8% total and 4.1 to 10.8% lipids.

Figure 2:
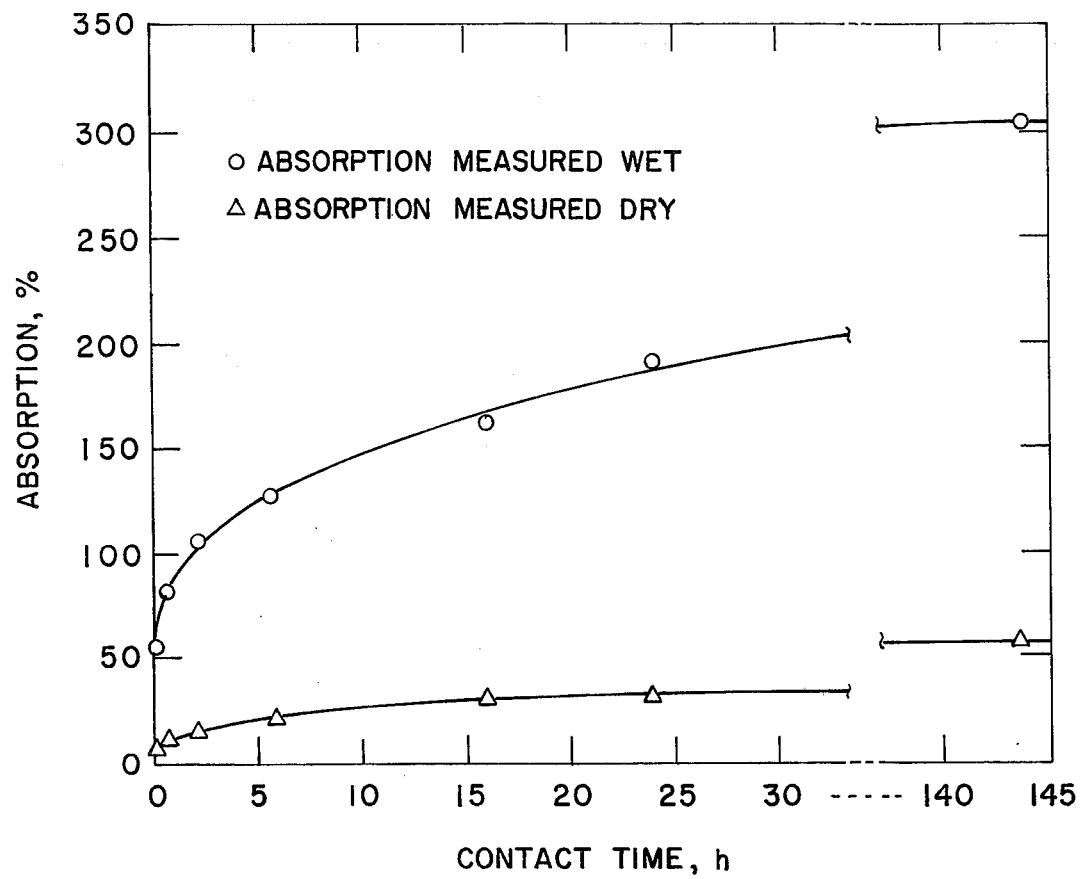
FIG. 2 is a graph illustrating the change in percent absorption as ordinate versus contact time in hours as abscissa.

The particle size effects on absorption rate expected from diffusion considerations were observed in all comparisons between chunk and ground samples. Chunk absorption was slower. Rate measurements also indicated that in the earlier time periods water absorption leads lipid absorption. The water and lipid absorption rates in ground polymer (75/25 PEO/PB) are illustrated in FIG. 2.

Absorbates extracted from representative samples that had absorbed significant amounts of lipids were shown by thin layer chromatography (TLC) to contain all three lipids, cholesterol, sodium cholate and lecithin. No quantitative measurement of the relative concentrations of these three compounds were made. However, qualitative examination of the TLC records indicates that they are probably in about the same proportions as they were in the model bile solutions.

The rate of absorption of ground polymer (1 mm) of Ex. 5 containing 75% by weight PEO and 25% HTPB was further tested with ox bile containing 15% lipids. The results are illustrated in the following table.

TABLE 2

| Contact Time | % Absorption Wet | % Absorption Dry | Ratio % Absorption Wet % Absorption Dry |
|---|---|---|---|
| 5 Min. | 82.52 | 4.69 | |
|  | 73.98 | 5.21 | ~ 17 |
|  | 77.42 | 3.97 | |
| 30 Min. | 105.86 | 12.50 | |
|  | 104.41 | 12.10 | ~ 9 |
|  | 105.85 | 12.15 | |
| 2 Hrs. | 145.48 | 17.74 | |
|  | 155.26 | 17.92 | ~ 8 |
|  | 150.61 | 19.08 | |
| 6 Hrs. | 228 | 27.16 | |
|  | 229 | 27.29 | ~ 8 |
|  | 226 | 26.18 | |
| 16 Hrs. | 271.7 | 32.18 | |
|  | 272.6 | 32.76 | ~ 8 |
|  | 248.2 | 33.21 | |
| 24 Hrs. | 227.33 | 31.74 | |
|  | 266.72 | 32.31 | ~ 7 |
|  | 199.57 | 31.26 | |
| 144 Hrs. | 362.3 | 38.62 | |
|  | 381.3 | 41.97 | ~ 9 |
|  | 335.2 | 37.44 | |

FIG. 1 shows that lightly cross-linked amorphous polymers composed primarily of hydrocarbon chains (Ex. 6, polybutadiene) cannot absorb very much of the lipids, bile acids, lecithin and cholesterol, from aqueous micellar solutions of them. The same is true of similar polymers composed primarily of hydrophilic chains (Ex. 4, polyethylene oxide). However, similar polymers composed of homogeneous mixtures of these two kinds of chains absorb significant amounts of these lipids. The capacity for lipid absorption appears to depend systematically on the relative proportions of the two types of chain, as shown in FIG. 1.

Absorption rates depend on polymer particle size. Even with small particles, a long time (excess of 144 hours) is needed to reach equilibrium (see FIG. 2). The ratio of lipid to water absorbed appears to be an interesting parameter. It appears possible that there is no selectivity in the polymer with regard to the three lipids present in the micellar solutions tested.

Further observations indicate that as absorption takes place (as in rate studies), water take-up leads lipid transfer. What is more, maximum water concentration (in the absence of lipids) is reached in 5 minutes. That maximum, however, is much less than when lipids are present (70–80%, versus over 300%). Therefore, lipids enhance the capacity of the polymer for water. Within the range tested, the concentration of lipids in the micellar solution does not exert a large effect on the amount of lipid absorbed by the polymer. Equilibrium (or near) absorption from 50% lipid solution was about 60%. With 15% solution, the corresponding value was 40%. It is possible, of course, that other composition features of the two solutions affect this result, since the former result was obtained with "model bile" of the previous work, and the later was with reconstituted dehydrated ox bile (commercial).

Thus, it appears that the absorption capacity of mixed chain polymers requires sufficient concentration of hydrophilic chain in the polymer to accommodate the lipid polar groups; then absorption capacity depends on the concentration of oleophilic chains. Initial support for this theory was obtained by calculations based on the data from the equilibrium absorption tests of the polymers of Ex.'s. 3 and 5 (see FIG. 1). Oleophilic chain concentration was taken to be the fraction of hydrocarbon prepolymer less functional groups. In Ex. 3, the hydrocarbon was Telagen U polybutadiene, and the oleophilic chain concentration contributed by it was 7.89%; the polymer of Ex. 5 contained 14.4% oleophilic chain from Butarez polybutadiene plus 34.8% from the DDI (dimer acid diisocynate) used; the total was 49.2%. Based on these values, absorptions are 1.205 gm lipid/gm oleophilic chain in Ex. 3 and 1.999 in Ex. 5.

Not only will some organic solvents (dioxane, others) extract absorbed lipids out of the polymer, so also will water. So far, the data seem to show a rapid leach rate (by water) at first, followed by a decreasing rate which appears to form an asymptotic approach to residual concentrations of about ⅓ the original concentration, whatever it was. Bile will extract oils from strictly hydrocarbon (olephilic) polymers which have been allowed to imbibe such oils from bulk. The shape of the absorption rate curves imply first-order kinetics.

The best mixed chain polymer made during this work (Ex. 5) was composed of 25 parts polydiene prepolymer and 75 parts polyethylene oxide prepolymer, plus curing agents. This polymer has been reproduced several times and performs reproducibly. When ground to a particle size of about 1 mm, it absorbs from 5 to 10% lipids from model bile in 5 minutes, about 35% in 2 hours, and 59% at equilibrium, which occurs somewhere around 144 hours.

There are reasons to expect that the ultimate capacity of this polymer family can be increased. It is believed that optimized cross-linking density will provide marked improvement in capacity. The second reason pertains to the proportions of the two kinds of chain in the polymer, and it is illustrated in FIG. 1. First, it should be noticed that not only are pure hydrocarbon (oleophilic) polymers poor absorbers under these conditions but also are pure hydrophilic polymers. The $$\frac{15 \text{ gm polymer}}{\text{dose}} \left(\frac{0.10 \text{ gm absorbed in 5 min.}}{\text{gm polymer}}\right) \left(\frac{1 \text{ gm cholesterol}}{100 \text{ gm abs.}}\right)$$

$$= \frac{0.015 \text{ gm cholesterol}}{\text{dose}}$$

$$= \frac{0.75 \text{ gm bile salts}}{\text{dose}}$$

As a comparison, 15 grams of a present commercial polymer (U-26) absorbs 6 grams of bile salts but does not absorb any cholesterol.

The lightly cross-linked, swellable, mixed chain polymers of the invention will find general use in the absorption of polar substituted large organic molecules. The polymer can be utilized in dialysis membranes to selectively pass lipo-proteins. Polar substituted steroid pharmaceuticals such as anti-inflammatory agents or fertility control drugs may be formulated as a stable solution within the network polymer. Since aqueous media can slowly leach the bound molecules from within the network polymers, such formulations can be utilized for oral ingestion to slowly release the medication within the G.I. tract. A network formulation containing a steroid drug could be encased within a pharmaceutically acceptable porous envelope such as silicone and implanted under the skin to slowly release the drug into the blood stream. If the network polymer demonstrated suitable biodegradability and the biodegraded by-products could be assimilated into the body, the envelope may not be required.

A clinical sampling device can be prepared to determine the level of lipids in aqueous body fluids such as blood. The fluid can be removed from the body and the amount of lipids absorbed by the polymer determined. In another technique, a porous-wall envelope of the polymer can be implanted into the body for a preselected absorption period and then removed for analysis of the amount and type of absorbed lipids.

It is to be understood that only preferred embodiments of the invention have been described, and that numerous substitutions, alterations, and modifications are all permissible without departing from the spirit and scope of the invention as defined in the following claims.

What is claimed is:

1. A lightly cross-linked, water-insoluble, swellable, polyurethane, network polymer comprising a cross-linked network of polymer segments consisting essentially of from 1 to 90% by weight of hydroxyl-terminated hydrophilic polyether chain segments, the remainder being hydroxyl-terminated oleophilic hydrocarbon polymer chain segments, a trihydroxy, organic cross-linking agent in an amount less than one cross-link for every 4,000 chain atoms of the network polymer and a substantially stoichiometric amount of diisocyanate curing agent, said segments containing no less than 25 backbone chain atoms and said polymer being in the form of particles having a diameter of no more than 1 mm, a swellability of no less than 2, an absorptivity on a dry basis of polar organic compounds of at least 10 percent, and a cross-link density of no more than one cross-link for every 4,000 backbone chain atoms.

2. A polymer in accordance with claim 1 in which the chain segments have molecular weights from 1,000 to 5,000.

3. A polymer according to claim 2 in which the oleophilic chain segments are selected from polymers of $C_2$ to $C_8$ monounsaturated aliphatic hydrocarbon monomers, $C_4$ to $C_8$ dienes or copolymers or saturated derivatives thereof.

4. A polymer according to claim 3 in which the oleophilic chain segments are liquid polymeric polybutadienes containing hydroxyl terminated groups and having a functionality from 1.8 to 2.5.

5. A polymer according to claim 4 in which the hydrophilic chain segments are selected from polyalkylene oxides having functional termination and a molecular weight from 1,000 to 5,000.

6. A polymer according to claim 5 in which the hydrophilic chain segment is a polyethylene oxide having hydroxyl termination.

7. A polymer according to claim 6 in which the chain segments are connected by condensation groups and the cross-links are formed by condensation groups.

8. A polymer according to claim 7 in which said groups are urethane groups.

9. A method of synthesizing a lightly cross-linked, water-insoluble network polymer having a swellability of no less than 2, an absorptivity on a dry basis of polar organic compounds of no less than 10, and a cross-link density of no more than one cross-link for every 4,000 backbone chain atoms comprising the steps of:
   forming a mixture of 1–75% by weight of hydroxyl-terminated polyether hydrophilic polymeric chain segments having at least 25 chain atoms in each segment and the remainder being hydroxyl-terminated oleophilic hydrocarbon polymeric chain segments containing at least 25 carbon atoms per segment;
   adding a trihydroxy organic cross-linking agent in an amount less than one cross-link for every 4,000 chain atoms of the final network polymer to said mixture and allowing said mixture to react with a substantially stoichiometric amount of a diisocyanate curing agent to form cross-links between said chain segments such that the swellability of the final polymer is at least 2 and the absorptivity is at least 10 percent; and
   removing the non-cross-linked soluble portion from said polymer by solvent extraction.

10. A method according to claim 9 in which the mixture is a solution of both sad chain segments in a common solvent.

11. A method according to claim 10 in which the oleophilic chain segment is a liquid polybutadiene polymer and the hydrophilic chain segment is a liquid polyethylene oxide polymer.

* * * * *